United States Patent [19]

Tolentino

[11] 4,332,956
[45] Jun. 1, 1982

[54] PROCESS FOR PREPARING ACYLOXYSILANES

[75] Inventor: Luisito A. Tolentino, Ballston Lake, N.Y.

[73] Assignee: General Electric Company, Waterford, N.Y.

[21] Appl. No.: 278,541

[22] Filed: Jun. 26, 1981

[51] Int. Cl.$^3$ .............................. C07F 7/08; C07F 7/04
[52] U.S. Cl. ................................................... 556/442
[58] Field of Search ........................................ 556/442

[56] References Cited

U.S. PATENT DOCUMENTS

| | | | |
|---|---|---|---|
| 2,017,000 | 8/1935 | Hintermaier | 556/442 X |
| 2,405,988 | 8/1946 | Barry | 556/442 |
| 2,537,073 | 1/1951 | MacKenzie et al. | 260/448.8 |
| 2,566,347 | 9/1951 | MacKenzie | 556/442 |
| 2,866,800 | 12/1958 | MacKenzie et al. | 556/442 |
| 3,700,714 | 10/1972 | Hamilton et al. | 260/448.2 B |
| 3,701,753 | 10/1972 | Shaw | 260/9 R |
| 3,792,071 | 2/1974 | Nitzsche et al. | 260/448.8 R |
| 3,974,198 | 8/1976 | Ashby | 260/448.2 E |
| 4,028,391 | 6/1977 | Foley | 260/448.2 D |
| 4,176,130 | 11/1979 | John et al. | 260/448.2 E |

FOREIGN PATENT DOCUMENTS 2801780  7/1979  Fed. Rep. of Germany ...... 556/442 UX

*Primary Examiner*—Paul F. Shaver
*Attorney, Agent, or Firm*—Ernest F. Chapman; Michael J. Doyle

[57] ABSTRACT

Acyloxysilanes are prepared by reacting a chlorosilane with an aliphatic carboxylic acid in a column at an elevated temperature wherein the aliphatic carboxylic acid in the vapor phase reacts with the chlorosilane in the column. The improvement comprises introducing the carboxylic acid into the column in a plurality of feed streams preferably at such a rate that the carboxylic acid exceeds 1.3 moles per gram atom of silicon-bonded chlorine in the column and removing low boiling reaction by-products and hydrogen chloride gas from the top of the column while collecting the acyloxysilane product dissolved in the aliphatic carboxylic acid at the bottom of the column. At least one feed stream of aliphatic carboxylic acid must be located above the chlorosilane feed stream. Aliphatic carboxylic acid is also provided from at least one source located below the chlorosilane feed stream, for example, from at least one feed stream located below the chlorosilane feed stream or from aliphatic carboxylic acid in a reboiler at the bottom of the column or both. In a preferred embodiment, methyltriacetoxysilane is prepared by reacting methyltrichlorosilane with acetic acid in a heated fractionation column.

29 Claims, No Drawings

PROCESS FOR PREPARING ACYLOXYSILANES

BACKGROUND OF THE INVENTION

The present invention relates to a process for producing acyloxysilanes, and more particularly, to an improved process for the continuous production of acyloxysilanes in a system which substantially increases capacity over prior art systems and forms recyclable hydrogen chloride.

Acyloxysilanes are well known cross-linking agents for one-part room temperature vulcanizable silicone rubber compositions. One common acyloxysilane cross-linking agent is methyltriacetoxysilane.

Acyloxysilane cross-linking agent has been made by the reaction of an appropriate chlorosilane with a carboxylic anhydride or with a carboxylic acid. One process for preparing acyloxysilanes by reacting a chlorosilane with a carboxylic acid or carboxylic acid anhydride in the presence of an iron complexing agent is disclosed in U.S. Pat. No. 3,974,198. In U.S. Pat. No. 3,974,198, an aliphatic carboxylic acid, such as glacial acetic acid, was added at the top of a distilling column to a refluxing mixture of chlorosilane in an organic solvent, such as benzene, containing an iron complexing agent. After the completion of the addition of the aliphatic carboxylic acid, the solvent was removed by distillation, and the acyloxysilane compound was eventually isolated from the mixture.

Aliphatic carboxylic acid in the vapor phase is passed upwards from the bottom of a column filled with Raschig rings countercurrent to a flow of chlorosilane in U.S. Pat. No. 4,176,130. However, in U.S. Pat. No. 4,176,130 only a limited amount of aliphatic carboxylic acid is introduced into the column so that the feed rate of the carboxylic acid does not exceed 1.3 moles per gram atom of silicon-bonded chlorine in the column. Thus, at most, only a very slight excess of aliphatic carboxylic acid is introduced into the column in U.S. Pat. No. 4,176,130. The liquid glacial acetic acid vaporizes as it enters the column, and the acetic acid vapor rises against the flow of the chlorosilane. When only a slight excess or less of the aliphatic carboxylic acid is used in the reaction, it is believed that much of the chlorosilane remains unreacted, and the column throughput is low. Furthermore, the passage of the aliphatic carboxylic acid vapor upwards only from the bottom of the column does not insure a sufficient amount of the carboxylic acid in the upper regions of the column where the chlorosilane is introduced into the column, to react with chlorosilane vapors in the upper regions of the column. Consequently, significant amounts of chlorosilane vapor can be lost or remain unreacted at the top of the column.

The formation of dimer at the bottom of the column is a significant side reaction that results from thermal decomposition of monomeric acyloxysilanes or from a reaction of the chlorosilane with acyloxysilane or both. The dimer is represented by the following formula:

$$R_n(R'COO)_{3-n}Si-O-Si(R'COO)_{3-n}R$$

wherein R and R' are alkyl radicals generally of 1 to about 8 carbon atoms and n is 1 to 3. When the reactants form dimer, it reduces the amount of acyloxysilane product. Thus, it is desirable to reduce the amount of dimer formed from the reaction, or to increase column throughput to provide commercial quantities of the acyloxysilanes even though the dimer is formed. It is also desirable to provide sufficient aliphatic carboxylic acid in the upper regions of the column to react with chlorosilane vapors before they escape or condense.

The continuous prior art processes are also disadvantageous insofar as low boiling contaminants generally accumulate in the column, and the low boiling contaminants reduce the column temperature. Accordingly, it is desirable to provide a process which eliminates this problem so that the column temperature can be maintained at a steady maximum temperature. In prior art processes, especially those using reduced pressure, where hydrogen chloride gas is produced as a by-product, it is necessary to neutralize the gas and thereby waste a valuable by-product. Accordingly, it is desirable to provide a process which recovers hydrogen chloride gas suitable for recycling and use in other processes.

SUMMARY OF THE INVENTION

It is the primary object of the present invention to provide an improved process for producing acyloxysilanes by reacting a chlorosilane with an aliphatic carboxylic acid in a column at an elevated temperature.

It is another object of the present invention to provide an improved process for producing acyloxysilanes by reacting a chlorosilane with an aliphatic carboxylic acid in a column at elevated temperatures, wherein the aliphatic carboxylic acid in the vapor phase is not only present in the lower regions of the column but is also present in the upper regions of the column.

It is an additional object of the present invention to provide an improved process for producing acyloxysilanes in a system which maintains the column temperature at a steady maximum temperature.

Still another object of the present invention is to provide a process for producing acyloxysilanes by reacting a chlorosilane with an aliphatic carboxylic acid in a column at an elevated temperature and at substantially atmospheric pressure.

Another object of the present invention is to provide a process for producing acyloxysilanes by reacting a chlorosilane with an aliphatic carboxylic acid in a column at an elevated temperature wherein the column capacity is substantially increased.

It is another object of the present invention to provide a process for producing acyloxysilanes by reacting a chlorosilane with an aliphatic carboxylic acid and recovering hydrogen chloride gas by-product.

In accordance with the foregoing objects, there is provided a process for producing acyloxysilane by reacting a chlorosilane with an aliphatic carboxylic acid in a column at an elevated temperature wherein the chlorosilane is introduced in the upper section of the column, the improvement comprising introducing the aliphatic carboxylic acid in the column above the chlorosilane feed stream and below the chlorosilane feed stream. Thus, the improvement embodies introducing aliphatic carboxylic acid into the column from a plurality of sources, at least one upper source of aliphatic carboxylic acid being a feed stream introduced above the chlorosilane and at least one lower source of aliphatic carboxylic acid being introduced below the chlorosilane. The lower source of aliphatic carboxylic acid is any aliphatic carboxylic acid introduced below the chlorosilane and includes a feed stream of aliphatic carboxylic acid located below the chorosilane feed stream, or aliphatic carboxylic acid refluxed into the column from a reboiler located at the bottom of the column or both, and the like. Hydrogen chloride gas generated as a byproduct of the reaction is collected from the upper section of the column.

Generally, the aliphatic carboxylic acid is in substantial excess of the chlorosilane reactant, that is, greater than 1.3 moles per gram atom of silicon-bonded chlorine, so that the aliphatic carboxylic acid acts as a solvent in the collection vessel or reboiler, and the reacting mixture becomes distributed throughout the column as a solution of the chlorosilane monomer in the aliphatic carboxylic acid. The product discharged from the lower end of the column is an aliphatic carboxylic acid solution of the acyloxysilane product. By the process of the present invention, column capacity is increased as much as about 14 to about 20 times that of the prior art processes, and chlorosilane in the upper region of the column, that is above the chlorosilane feed port, reacts with aliphatic carboxylic acid introduced above the chlorosilane feed port. This increase in column capacity increases the efficiency of the process and results in substantial economy in the production of the acyloxysilanes and prevents loss of unreacted chlorosilane. Generally, the chlorosilanes which may be used in the process of the present invention, have the general formula:

$R_nSiCl_{4-n}$ wherein R is an alkyl radical having from 1 to about 8 carbon atoms, an aryl radical, a hydrogen atom or mixtures of the foregoing, and n varies from 0 to 3. Other chlorosilanes which may be employed in the process of this invention are those having the general formula:

$Cl_{3-b}SiR_bR'R_bSiCl_{3-b}$ where R represents the same or different substituted or unsubstituted hydrocarbon radicals having from 1 to about 8 carbon atoms, R' represents a bivalent hydrocarbon radical, for example, an ethylene or phenylene radical, and b is 1 or 2.

DETAILED DESCRIPTION OF THE INVENTION

In the chlorosilanes having the formula:

$R_nSiCl_{4-n}$ for producing acyloxysilanes in accordance with the process of the present invention, R may be the same or different substituted and unsubstituted hydrocarbon radicals having from 1 to about 8 carbon atoms, the same or different and unsubstituted aryl radicals having up to about 3 rings, hydrogen atoms and mixtures of the foregoing, and n may be 0, 1, 2 or 3. Examples of various specific hydrocarbon radicals and classes of hydrocarbon radicals represented by R in the formula above are alkyl radicals, such as methyl, ethyl, propyl, isopropyl, butyl, sec-butyl, octyl, and 2-ethylhexyl radicals; alkenyl radicals such as vinyl, and allyl radicals; the hexadienyl radicals; cycloalkyl radicals, such as cyclopentyl, cyclohexyl, and cycloheptyl radicals; cycloalkenyl radicals; aromatic hydrocarbon radicals, such as phenyl, and naphthyl radicals; aralkyl radicals, such as benzyl and phenylethyl radicals; alkaryl radicals, such as tolyl and dimethylphenyl radicals; and the like. Substituted hydrocarbon radicals include halogenated hydrocarbon radicals, such as chloromethyl, 3-chloropropyl, 3,3,3-trifluoropropyl radicals and the like.

The chlorosilanes having the general formula:

$Cl_{3-b}SiR_bR'R_bSiCl_{3-b}$ which may be used in the process of the present invention for producing acyloxysilanes, include those represented by the formula wherein R may be the same or different substituted or unsubstituted hydrocarbon radicals having from 1 to about 8 carbon atoms. R' is a bivalent hydrocarbon radical, such as, ethylene or phenylene radical; and b is 1 or 2. The particular chlorosilane or mixtures of chlorosilanes used in the process of the present invention are not critical as long as they form acyloxysilanes by reacting with aliphatic carboxylic acid in the process of the present invention.

The aliphatic carboxylic acids used to produce the acyloxysilanes in the process of the present invention have the formula:

R"COOH wherein R" is an alkyl radical having 1 to about 8 carbon atoms or hydrogen. For example, R" may include methyl, ethyl, propyl, isopropyl, butyl, isobutyl, pentyl, hexyl, 3-methylpentyl and the like. The aliphatic carboxylic acids used in the process of the invention include acetic acid, propionic acid, butyric acid, formic acid, valeric acid and dimethyl acetic acid. The aliphatic carboxylic acid must be vaporizable since the carboxylic acid is vaporized and passes upward in the vapor phase in the column. In preferred embodiments, the aliphatic carboxylic acid is in the vapor state in at least one of the feed streams or feed ports before it is introduced into the column and/or the reboiler. Any suitable means may be used for vaporizing the aliphatic carboxylic acid prior to feeding the aliphatic carboxylic acid vapor into the column. For example, the aliphatic carboxylic acid may be fed to a heat exchanger at a controlled rate; the carboxylic acid is then vaporized in the heat exchanger; and the aliphatic carboxylic acid vapor is then fed into the reboiler (collection vessel) and/or the column. Any suitable device may be used to regulate the addition of the aliphatic carboxylic acid into the heat exchanger, into the reboiler or into the column. In one embodiment, the bottom feed of aliphatic carboxylic acid, that is, the source of carboxylic acid in the column below the chlorosilane feed stream, is provided by heating the carboxylic acid charged to the reboiler in a stoichiometric excess prior to the start-up of the process, the heating of the carboxylic acid in the reboiler causing refluxing vapors of the carboxylic acid at least in the lower regions of the column below the chlorosilane feed. In the present invention, liquid aliphatic carboxylic acid may be fed into the plurality of feed streams, that is, into the column or into the column and reboiler (collection vessel); aliphatic carboxylic acid vapor may be fed into the plurality of feed streams, that is, into the column or into the column and reboiler (collection vessel); or a mixture of liquid and vapor aliphatic carboxylic acid may be fed into the plurality of feed streams, that is, into the column or into the column and reboiler, and the like. It is also possible to use mixtures of aliphatic carboxylic acids in the process of the present invention, that is, for example a $C_5$ carboxylic acid in one feed stream and a $C_2$ carboxylic acid in another feed stream (auxiliary feed stream), or a mixture of C$_5$ carboxylic acid and C$_2$ carboxylic acid in each of the plurality of feed streams.

In the broadest aspect of the invention, aliphatic carboxylic acid is fed into the column above the chlorosilane feed and below the chlorosilane feed. Thus, the aliphatic carboxylic acid in the column is derived from a plurality of sources at least one of which is above the chlorosilane feed and at least one of which is below the chlorosilane feed.

In the process for producing acyloxysilanes in accordance with the process of the present invention, the improvement comprises introducing aliphatic carboxylic acid into the column from at least two locations, positions or sources, at least one being above the chlorosilane feed and at least one being below the chlorosilane feed. In preferred embodiments, carboxylic acid is introduced into the column or into the column and reboiler, at such a rate that the carboxylic acid exceeds 1.3 moles per gram atom of silicon-bonded chlorine in the column. Column capacity is increased by as much as 14 to 20 times by introducing the carboxylic acid into the column at a rate wherein the carboxylic acid exceeds 1.3 moles per gram atom of silicon-bonded chlorine in the column. In accordance with the process of the present invention, the introduction of aliphatic carboxylic acid into the column above the chlorosilane feed stream is critical, and it is used as an auxiliary supply of carboxylic acid in the column to complement the carboxylic acid provided from a suitable source below the chlorosilane feed stream. In preferred embodiments, a substantial excess of aliphatic carboxylic acid, that is, that amount which exceeds 1.3 moles per gram atom of silicon-bonded chlorine in the column, is introduced into the column, into the reboiler, or into the column and reboiler, the silicon-bonded chlorine being the chlorine content of the chlorosilane introduced into the column and generally flowing countercurrent to that aliphatic carboxylic acid introduced into the column above or below the chlorosilane feed stream.

In preferred embodiments, the total aliphatic carboxylic acid is introduced into the column or into the column and reboiler at such a rate that the ratio of carboxylic acid to chlorosilane is between about 1.35 and about 2.1 gram moles of carboxylic acid per gram atom of silicon-bonded chlorine. The total amount of aliphatic carboxylic acid, that is, the amount of acid in all streams, may be expressed as a stoichiometric excess of about 10 mole % to about 60 mole % of the amount of chlorosilane in certain preferred embodiments. In one of the most preferred embodiments, the aliphatic carboxylic acid is introduced at such a rate that the ratio of carboxylic acid to chlorosilane is about 1.6 to about 1.7 gram moles of aliphatic carboxylic acid per gram atom of silicon-bonded chlorine. When the amount of aliphatic carboxylic acid exceeds 1.3 moles per gram atom of silicon-bonded chlorine in the column, there is an excess of aliphatic carboxylic acid in the column sufficient to cause a more complete reaction of the carboxylic acid with the chlorosilane, and there is an increase in column capacity of about 14 to about 20 times over those embodiments wherein the aliphatic carboxylic acid/chlorosilane ratio is less than about 1.3 moles per gram atom of silicon-bonded chlorine in the column. Furthermore, when part of the aliphatic carboxylic acid is introduced into the column at a region above the chlorosilane feed stream, that is, by means of an auxiliary feed stream, aliphatic carboxylic acid is provided in the upper section, region or portion of the column to react with any chlorosilane vapors rising in the column. As used herein, upper section region or portion of the column generally specifies the upper one-half of the column, and more preferably, the upper one-fourth of the column.

The feed stream of aliphatic carboxylic acid introduced above the chlorosilane feed stream may be designated herein as the auxiliary feed stream or upper feed stream of aliphatic carboxylic acid. The total number of feed streams is not critical, however, there must be at least one source for aliphatic carboxylic acid in the column below the chlorosilane feed stream, and there must be an auxiliary aliphatic carboxylic acid feed stream located above the chlorosilane feed stream. The aliphatic carboxylic acid in the column below the chlorosilane feed stream can be a stoichiometric excess of the carboxylic acid already present in the column from heating and/or refluxing carboxylic acid in the reboiler prior to or concurrent with starting the chlorosilane feed, and/or carboxylic acid can also be provided from various feed streams in the column and/or the reboiler as desired, as well as combinations of the foregoing, and the like. Thus, in one aspect of the invention, the improvement comprises providing at least one feed of carboxylic acid above the chlorosilane feed when an excess of acid is already present in the column from heating and refluxing before the initiation of the chlorosilane feed.

Although it is not critical, in certain aspects of the present invention, it is also possible to provide a plurality of chlorosilane feed streams. The plurality of aliphatic carboxylic acid feeds can be supplied with acid from a common reservoir and common supply conduits, or they can be supplied with acid from separate reservoirs and separate supply conduits used in conjunction with vaporizing means where appropriate, that is with a system which converts aliphatic carboxylic acid into a vapor state.

The specific location of the feed streams in the column and/or the reboiler is not critical as long as aliphatic carboxylic acid is provided in the column above the chlorosilane feed and below the chlorosilane feed and as long as there is one chlorosilane feed stream, and one skilled in the art can easily determine the appropriate location of the feed streams or other sources of the reactants to provide optimum results.

In preferred embodiments, the main stream of aliphatic carboxylic acid is fed into the column at or near the base of the column or into the reboiler, and the auxiliary stream of aliphatic carboxylic acid is fed into the column at or near the top of the column below the overhead condenser. In certain other preferred embodiments, greater amounts of the aliphatic carboxylic acid are introduced above the chlorosilane than below the chlorosilane feed stream. For example, in certain preferred embodiments, about 2% to about 40% by volume of the aliphatic carboxylic acid may be introduced in the auxiliary feed stream or streams above the chlorosilane feed stream, and the balance of the aliphatic carboxylic acid is introduced below the chlorosilane feed stream. In one specific example 25% by volume of the acid is introduced above and 75% by volume of the acid is introduced below the chlorosilane feed stream. In certain other preferred embodiments, about 60% to about 90% by volume of the aliphatic carboxylic acid may be introduced in the auxiliary feed stream or streams above the chlorosilane feed stream, and the balance of the aliphatic carboxylic acid is introduced below the chlorosilane feed stream. The chlorosilane is fed at a controlled rate at a point sufficiently below the top of the column to permit the reaction of the chlorosilane and the aliphatic carboxylic acid. Heat is applied to the reboiler to control the boil-up rate of the column and the pressure drop across the column. A small amount of condensate reflux from the overhead condenser is removed at the top of the column to eliminate low boiling impurities that would otherwise lower the temperature in the column. By-product hydrogen chloride gas is removed from the overhead condenser and passes to suitable recovery equipment.

In accordance with the invention, the process for producing acyloxysilanes is carried out in a packed column equipped with a reboiler, overhead condenser and, optionally, a heat exchanger for vaporizing the carboxylic acid. Generally, the column used for the process of the invention is not critical and may be any packed column which can also be used for fractionation distillations. Low boiling reaction products and contaminants are distilled and are collected after they are condensed in the overhead condenser. Hydrogen chloride gas is removed from the overhead condenser and used in other processes. The removal of the low boiling contaminants and reaction by-products maintains column temperatures at a maximum.

The acyloxysilane product forms in the packed column as a result of the reaction between the chlorosilane passing generally downward in the column and aliphatic carboxylic acid vapor passing countercurrent thereto in an upper direction in the column. The acyloxysilane product passes down the column to the reboiler, and a solution of acyloxysilane in aliphatic carboxylic acid can be continuously or intermittently drawn from the reboiler (collector vessel). Subsequent distillation of the solution of carboxylic acid and acyloxysilane generally provides an acyloxysilane containing less than 10.5 ppm chloride (the sum of unreacted chlorosilane and hydrogen chloride).

The reactant flow pattern in the reaction column is not critical, however, there is generally a countercurrent flow of aliphatic carboxylic acid and the chlorosilane in order to drive the reversible reaction to completion. That is, the main stream of aliphatic carboxylic acid reactant is introduced at the base of the column or the reboiler or both and moves upward as a vapor of the aliphatic carboxylic acid while chlorosilane and partly acyloxylated silanes move down the column in the liquid phase. The chlorosilane, for example, methyltrichlorosilane, reactant first passes in an upward direction in the column because of its lower boiling point and continues in its passage upward in the column until one of the chlorines in the chlorosilane has reacted with the aliphatic carboxylic acid to increase the boiling point of the monomer at which point the movement of the material in the column is reversed, and it begins a downward passage in the column. It is for this reason that the chlorosilane is fed to the column at a point sufficiently below the top of the column to allow partial reaction of the chlorosilane with the carboxylic acid vapor in the column while the chlorosilane monomer is passing upward in the column. It is also for this reason that the auxiliary aliphatic carboxylic acid feed stream is provided above the chlorosilane feed stream to insure a sufficient amount of aliphatic carboxylic acid to react with the rising vapors of chlorosilane and to provide aliphatic carboxylic acid to supplement the aliphatic carboxylic acid vapor rising in the column. The position of the chlorosilane feed stream can be easily adjusted to obtain optimum reaction conditions for the particular distillation column, the particular reactants, products and by-products and other equipment used to carry out the process. Although it is not critical, generally the flow pattern of the reactants in the reaction column is countercurrent below the chlorosilane feed point, and the flow pattern is both countercurrent and co-current above the chlorosilane feed point in the column. One skilled in the art can provide various combinations of and locations of feed streams to carry out the process of the present invention without undue experimentation.

The length of the column is not critical, and generally, the height of the column is limited solely by economic considerations. In prefered embodiments, the column is packed with suitable packing. Most conventional corrosion-resistant packing materials may be used. One type of preferred packing material is a chemical porcelain material known as Intalox saddles. Other packing materials include Raschig rings and glass helices.

In the process of the present invention for producing acyloxysilanes, the reaction of the chlorosilane with aliphatic carboxylic acid may be carried out at any suitable pressure. In preferred embodiments, the reaction is carried out at atmospheric pressure, that is at about 760 mm Hg. However, the process may also be carried out in accordance with the present invention by reducing the pressure below atmospheric pressure, and in such cases the reaction is carried out at pressures between about 10 mm Hg. and about 760 mm Hg. It is also possible to carry out the process of this invention at pressures greater than atmospheric pressure, however, increased reboiler temperatures are generally required at elevated pressures.

The solutions in the column and the reboiler are generally maintained at their boiling point, that is, the column must be operated as a distillation column. Acyloxysilanes have high boiling points, for example, methyltriacetoxysilane boils at 200° C. at 760 mm Hg., and acyloxysilanes usually decompose at temperatures above their atmospheric boiling points. As explained above, boiling of the solutions in the column and the reboiler at practical and tolerable temperatures can be affected by reducing the absolute pressure. Furthermore, the boiling can be affected by introducing a lower boiling material, such as a solvent. In the process of the present invention, the aliphatic carboxylic acid in stoichiometric excess of the chlorosilane reactant acts as a solvent so that the reacting mixture and products formed therefrom are a solution of the silane monomer and the product in the aliphatic carboxylic acid, such as acetic acid. Thus, the product is discharged from the reboiler as a solution of the acyloxysilane in aliphatic carboxylic acid. The amount of excess aliphatic carboxylic acid over the chlorosilane reactant in the column feed stream determines the composition and boiling point of the solution in the reboiler, and consequently, determines the rate of formation of undesirable dimer in the reboiler.

Generally, the chlorosilane is reacted with the aliphatic carboxylic acid at a temperature which corresponds or substantially corresponds to the boiling point of the carboxylic acid used under prevailing conditions of pressure in the column. In preferred embodiments, the temperature of the column is maintained between about 95° C. to about 125° C. Furthermore, in preferred embodiments, the temperature in the column is maintained in gradients throughout the column, the temperature at the top of the column being lower than the temperature at the bottom of the column. Under one set of preferred reaction conditions, the temperature is maintained at reaction gradients throughout the column, the temperature at the top of the column being the lowest temperature and maintained at about 95° C. to about 100° C., and the temperature at the bottom of the column being the higher temperature and maintained at about 120° C. to about 125° C. Generally, the temperatures in the column are not controlled directly. A particular temperature depends upon the particular ingredients, such as the acid and the silane, and the pressure used in the system.

For economic reasons and in preferred embodiments, the process for the production of acyloxysilanes in general, and more specifically, for the production of methyltriacetoxysilane from the reaction of methyltrichlorosilane and acetic acid, is carried out as a continuous process wherein at least two feed streams of acetic acid are continuously fed into the vertical packed column or the vertical packed column and the reboiler, and a stream of chlorosilane is continuously fed into the column and passed downward therein, and wherein hydrogen chloride gas and low boiling reaction products are removed from the top of the distillation column. The acyloxysilane and unreacted acid are collected at the bottom of the column in a collecting vessel or reboiler and removed continuously therefrom. The acyloxysilane may then be separated from the acid by any suitable means, such as by distillation.

The following specific examples describe the process of this invention. They are intended for illustrative purposes only and should not be construed as limiting the present invention.

EXAMPLE 1

A glass column having a 7.6 cm (3 inch) internal diameter was constructed of nine 30.5 (12 inch) lengths of glass pipe alternated with nine 7.6 cm×3.8 cm (3 inch×1.5 inch) glass reducing crosses. Four packing support plates of single bubble cap design supported the column packing material which, in the case of this example, was 0.95 cm (⅜ inch) chemical porcelain saddles, to provide a total of 432.8 cm (14.2 feet) of packing material in the glass column. The porcelain, chemical stoneware tower filling materials used in this example were Intalox saddles (Intalox is a trademark of U.S. Stoneware Company). Additional 7.6 cm×3.8 cm reducing crosses were installed at the base of the column and at the top of the column without packing material.

The side flanges of the reducing crosses were equipped with thermal wells containing thermocouples, devices for sampling liquids at that point of the column, and feed tubes as desired to provide a temperature profile of the column, samples of the liquid in the column every 55.88 cm (22 inches), and flexibility of reactant feed points respectively. The column was jacketed, and the jacket was heated with electrical resistance heating tape to minimize heat loss from the column. Thermocouples in the annular jacket space indicated the jacket temperature. The jacket was suitably insulated to prevent heat loss.

A reboiler installed below the column was a 20 liter glass flask heated wtih an electrical mantel and equipped with a thermal well containing a thermocouple, a 7.6 cm (3 inch) top flange connecting the flask to the column and a top flange for pressure measurement. The reboiler flask was equipped with a bottom outlet for discharge of the product, and adjustable overflow pipe to control the liquid level in the reboiler flask. A collection flask was provided to collect the product from the reboiler flask, and the collection flask was equipped with a pressure equallizing line to the reboiler so that the collection flask could be held at the same pressure as the reboiler flask.

The top of the column was equipped with a reflux splitter, a water-cooled condenser and a brine-cooled condenser for cooling to −10° C. The uppermost part of the column was the brine-cooled condenser, and hydrogen chloride gas was removed from the brine-cooled condenser by means of a pipe to a recycling system which would permit the use of the hydrogen chloride gas. The column was equipped with auxiliary equipment including a pump for feeding chlorosilane reactant at a variable controlled rate through a feed tube located 256.0 cm (8.4 feet) below the top of the packing with the tube discharging to the center of the 7.6 cm reaction column. A second variable rate controlled pump was provided to feed the aliphatic carboxylic acid through an oil heated heat exchanger where the aliphatic carboxylic acid was vaporized so that the acid could be fed to the base of the column in vapor form. A third variable rate controlled pump was provided to feed the aliphatic carboxylic acid in liquid form to the top of the column. Multiple temperature measurement means, column pressure drop measurement means and means for measuring the feed of reactants and collection of product were also provided.

About 75% of the acetic acid was introduced to the base of the column in the vapor phase and about 25% of the acetic acid was introduced at the top of the column in a liquid form at 65° C. for a total input of 7.25 Kg (16 lbs.)/hour. The column pressure drop was 0.74 inches of water at 39.2° F. The sampling data for the ionic chloride, acetic acid, acetic anhydride, methyltrichlorosilane, dichlorosilane, monochlorosilane, methyltriacetoxysilane and dimer were taken at various column heights. The data is recorded in Table 1 below where, except as otherwise indicated, all data is recorded in percentages (based upon the area of the curve in gas chromatographic analysis).

TABLE 1

| SAMPLE POINT (cm) | TEMP. °C. | CHLORIDE | ACETIC ACID | ACETIC ANHYDRIDE | MeSiCl$_3$[1] | SiCl$_2$ | SiCl | MTAS[2] | DIMER |
|---|---|---|---|---|---|---|---|---|---|
| CONDENSER | 89 | — | — | — | — | — | — | — | — |
| 12.2 | 100 | — | — | — | — | — | — | — | — |
| 70.1 | 106 | — | — | — | — | — | — | — | — |
| 106.7 | 108 | 5.4% | 92% | 0.2% | 1.4% | 0.01% | 0 | 2% | 0.2% |
| 161.5 | 109 | 2.3% | 95% | 0.2% | 0.1% | TRACE | 0 | 3% | 0.5% |
| 213.4 | 114 | 3.2% | 84% | 0.1% | 0.2% | TRACE | 0 | 11.3% | 0.7% |
| 256.0 | 119 | 3.7% | 80% | 0.1% | 0.5% | 0.05% | 0 | 14.4% | 0.7% |
| 313.9 | 122 | 72.0% | — | 0.2% | 0 | 0 | 0 | — | — |

TABLE 1-continued

MEASUREMENTS AND SAMPLING DATA AT VARIOUS POINTS IN THE
SYSTEM FOR THE PRODUCTION OF METHYLTRIACETOXYSILANE

| SAMPLE POINT (cm) | TEMP. °C. | CHLORIDE | ACETIC ACID | ACETIC ANHYDRIDE | MeSiCl$_3$[1] | SiCl$_2$ | SiCl | MTAS[2] | DIMER |
|---|---|---|---|---|---|---|---|---|---|
| 350.5 | 123 | 9.0% | 89% | 0.2% | 0 | 0 | 0 | 9.8% | 0.3% |
| 405.4 | 123 | 5.0% | 89% | 0.4% | 0 | 0 | 0 | 9.8% | 0.3% |
| 432.8 | — | 2.0 | 88% | 0.7% | 0 | 0 | 0 | 10.8% | 0.4% |
| REBOILER | 140 | 3.0 | 45% | 1.0% | 0 | 0 | 0 | 50.0% | 3.4% |

[1]Methyltrichlorosilane
[2]Methyltriacetoxysilane

The overhead distillate in Example 1 had a methyltrichlorosilane content of about 2 to about 2.5%. It can be seen from the data in Table 1 that when the acetic acid was introduced at two different areas in the column, acceptable concentrations of the methyltriacetoxysilane product dissolved in acetic acid was obtained by the process of the present invention. Thus, although the acetic acid is fed at or near the bottom of the column in the vapor phase, it is possible to complement the excess acetic acid fed into the column by introducing liquid acetic acid into other regions of the column including the top of the column. In Example 1, 25% of the acetic acid was introduced into the top of the column in a liquid phase, and 75% of the acetic acid was introduced into the bottom of the column in the vapor phase.

EXAMPLE 2

In a glass column and under conditions similar to those discussed above for Example 1, 600 grams of glacial acetic acid in a 1-liter reboiler was heated to reflux in a packed column having a diameter of 2.54 cm (1.0 inch). The glass column was 121.9 cm (4 feet) long and was fitted at the top with a condenser maintained at −20° C. Methyltrichlorosilane liquid was fed into the glass column at a feed point 22.86 cm (9 inches) as measured from the top of the column at a rate of 1.1 gram per minute. Acetic acid at 20% stoichiometric excess over the methyltrichlorosilane was divided into two feed streams. About 80% of the acetic acid was introduced into the column at a feed port located 7.62 cm (3 inches) at the rate of 1.4 grams/minute in the form of vapor. The balance of the acetic acid was fed as liquid into the reboiler. Steady state was reached within two hours. A temperature of 122° to 135° C. prevailed in the reboiler. At the end of the 7 hour run, the residue after distillation of excess acetic acid at 20 mm Hg and keeping the pot temperature below 110° C., showed the following product composition as measured by area of the curve from the gas chromatograph:

| Acetic Acid | 0.5% |
|---|---|
| Methyltriacetoxysilane | 86.0% |
| Dimethyltetraacetoxysiloxane | 13.0% |
| High Boiling Fraction | 0.5% |

The ionic chloride content was 71 ppm.

EXAMPLE 3

In a 500-mil. reboiler (flask), 275 grams of glacial acetic acid was heated to reflux in a 1.23 meter×2.54 cm (diameter) pyrex packed column fitted with a condenser maintained at −20° C. Liquid methyltrichlorosilane was supplied at the 22.9 cm (9-inch) feed point (as measured from the top of the column) at 1 g/min while acetic acid was fed at the 7.6 cm (3-inch) point (as measured from the top of the column) at 2 g/min. At the end of the 7-hour run, distillation of excess acetic acid at 20 mm Hg. gave the following product composition as analyzed by gas chromatography:

| Acetic Acid and Acetic Anydride | 10% |
|---|---|
| Methyltriacetoxysilane | 85% |
| Dimethyltetracetoxysilane | 2% |
| High Boiling Fraction | 3% |

There was no detectable ionic chloride.

EXAMPLE 4

Following the procedure as described in Example 3, liquid methyltrichlorosilane at 1 g/min. and acetic acid at 2 g/min. were fed at the 61 cm. (24 inch) and 7.6 cm. (3 inch) feed points (as measured from the top of the column) respectively. After 7 hours, distillation of excess acetic acid gave the following product composition:

| Acetic Acide | 1% |
|---|---|
| Methyltriacetoxysilane | 96% |
| Dimethyltetracetoxysilane | 0.5% |
| High Boiling Fraction | 2.5% |

There was no detectable ionic chloride.

EXAMPLE 5

Using the procedure described in Example 3 methyltrichlorosilane at 1 g/min. was fed as a vapor at the 61 cm. (24-inch) point while liquid acetic acid was supplied at 2 g/min. at the 7.6 cm. (3-inch) point. After 7 hours, the stripped product gave the following product composition:

| Acetic Acid | 1% |
|---|---|
| Methyltriacetoxysilane | 95% |
| Dimethyltetraacetoxysilane | 1.5% |
| High Boiling Fraction | 2.5% |

There was no detectable ionic chloride.

The data of Examples 3, 4 and 5 illustrate that the process of the present invention can be carried out by feeding the aliphatic carboxylic acid into the column from the reboiler by heating the carboxylic acid in the reboiler, thereby causing the carboxylic acid vapor to pass into the column below the chlorosilane feed stream by refluxing, and by feeding a stream of carboxylic acid into the column above the chlorosilane feed stream.

In accordance with at least some of the objects of the invention, acyloxysilanes have been prepared by reacting a chlorosilane with an aliphatic carboxylic acid in a column at an elevated temperature by introducing the aliphatic carboxylic acid into the column in a plurality of streams. In at least portions of the column, the aliphatic carboxylic acid in the vapor phase passes upward from the bottom of the column countercurrent to the flow of the chlorosilane passing downward from the top of the column. Because of the auxiliary feed stream of acetic acid at the top of the column, chlorosilane vapors in the top portions or regions of the packed column react with the acetic acid in the top of the column. Low boiling reaction by-products and hydrogen chloride gas are removed from the top of the column while the acyloxysilane product dissolved in acetic acid is accumulated at the bottom of the column.

When compared with the prior art processes which introduce carboxylic acid into the column in only one feed stream in amounts less than 1.3 mole per gram atom of silicon-bonded chlorine in the column, the process of the present invention permits not only a 14 to 20 fold increase in column capacity over the processes of the prior art, but also utilizes a greater amount of the column for the reaction. The larger capacity of the process of the present invention results from higher column temperatures, greater vapor density and increased liquid loading in a reaction column operated at atmospheric pressure and an increased amount of aliphatic carboxylic acid above the chorosilane feed stream in the column.

While the invention has been described with respect to preferred embodiments, it will be apparent that certain modifications and changes can be made without departing from the spirit and scope of the invention, and therefore, it is intended that the foregoing disclosure be limited only by the claims appended hereto.

What is claimed is:

1. In a process for producing acyloxysilanes by reacting a chlorosilane with an aliphatic carboxylic acid in a column at an elevated temperature wherein the chlorosilane is fed into the column, aliphatic carboxylic acid passes upward in the column from a source below the chlorosilane feed, and hydrogen chloride gas is removed from the column, the improvement comprising introducing aliphatic carboxylic acid into the column above the chlorosilane feed.

2. The process of claim 1 comprising heating aliphatic carboxylic acid in a reboiler at a temperature which causes the carboxylic acid to reflux and thereby pass upward in the column.

3. The process of claims 1 or 2 comprising providing the aliphatic carboxylic acid in a stoichiometric excess of the chlorosilane.

4. In a process for producing acyloxysilanes by reacting a chlorosilane with an aliphatic carboxylic acid in a column at an elevated temperature wherein the chlorosilane is introduced in a feed stream in the column, and hydrogen chloride gas is removed from the column, the improvement comprising introducing a plurality of feed streams of the aliphatic carboxylic acid, one upper feed stream of aliphatic carboxylic acid being introduced at any point in the column above the chlorosilane feed stream and at least one lower feed stream of aliphatic carboxylic acid being introduced at any point below the chlorosilane feed stream.

5. The process of claim 4 comprising introducing aliphatic carboxylic acid in a reboiler located at the bottom of the column; heating the aliphatic carboxylic acid in the reboiler at a temperature which causes the carboxylic acid to form a vapor; and introducing the vapor into the column.

6. The process of claim 4 comprising heating an excess of aliphatic carboxylic acid in a reboiler at the bottom of the column at a temperature which causes the carboxylic acid to form a vapor and introducing the vapor into the column.

7. The process of claim 4 comprising introducing aliphatic carboxylic acid in a feed stream at a point in the column below the chlorosilane feed stream.

8. The process of claim 4 comprising introducing aliphatic carboxylic acid below the chlorosilane feed stream in reboiler located at the bottom of the column and into the column below the chlorosilane feed stream.

9. The process of claim 4 further comprising heating the aliphatic carboxylic acid to vaporize the acid and feeding the aliphatic carboxylic acid as a vapor into at least one of the feed streams.

10. The process of claim 4 comprising providing the aliphatic carboxylic acid in a stoichiometric excess of the chlorosilane.

11. The process of claims 4 or 10 wherein the aliphatic carboxylic acid is introduced at a stoichiometric excess of about 10 mole % to about 60 mole % of the amount of chlorosilane.

12. The process of claims 4 or 10 wherein the carboxylic acid is introduced into the column at such a rate that the ratio of carboxylic acid to chlorosilane is between about 1.35 and about 2.1 gram moles of carboxylic acid per gram atom of silicon-bonded chlorine.

13. The process of claim 4 further comprising operating the column at about 760 mm Hg pressure.

14. The process of claim 4 further comprising maintaining the temperature of the column between about 95° C. to about 125° C.

15. The process of claims 4 or 14 wherein the temperature is maintained in gradients throughout the column, the temperature at the top of the column being lower than the temperature at the bottom of the column.

16. The process of claim 4 further comprising reducing the temperature of the column above the upper feed stream of aliphatic carboxylic acid to at least −10° C.

17. The process of claim 4, further comprising reducing the temperature of the column above the upper feed stream of aliphatic carboxylic acid to about −20° C. to about −30° C. by providing a condenser and removing hydrogen chloride gas from the condenser.

18. The process of claim 1 wherein the same aliphatic carboxylic acid is fed into the plurality of feed streams.

19. A process for the continuous production of methyltriacetoxysilane from methyltrichlorosilane and acetic acid, comprising:
 (a) feeding a stream of methyltrichlorosilane into the upper section of a heated column whereby a substantial amount of the methyltrichlorosilane passes downward in the heated column;
 (b) introducing acetic acid above the stream of methyltrichlorosilane;
 (c) introducing acetic acid below the stream of methyltrichlorosilane, whereby acetic acid reacts with methyltrichlorosilane to form low boiling reaction products, hydrogen chloride, methyltriacetoxysilane and reaction by-products;
 (d) condensing vapors of acetic acid and low boiling reaction products at the top of the column at a point above the acetic acid feed stream by means of a condenser and removing hydrogen chloride gas from the condenser; and
 (e) collecting and continuously removing the methyltriacetoxysilane, unreacted acetic acid and reaction by-products from a reboiler at the bottom of the column, the reboiler being maintained at a temperature higher than the temperature of the column.

20. The process of claim 19 wherein the acetic acid is introduced into the column in a stoichiometric excess relative to the methyltrichlorosilane.

21. The process of claims 19 or 20 wherein the acetic acid is introduced into the column at such a rate that the acetic acid to methyltrichlorosilane ratio is about 1.6 to about 1.7 gram moles of acetic acid per gram atom of silicon-bonded chlorine.

22. The process of claim 19 further comprising operating the column at about 760 mm Hg. pressure.

23. The process of claim 19 further comprising maintaining the temperature of the column between about 95° C. to about 125° C.

24. The process of claim 19 wherein the acetic acid is used in a stoichiometric excess of at least 1.3 moles of acetic acid per gram atom of silicon-bonded chlorine.

25. The process of claim 19 wherein the condenser is maintained at a temperature of −10° C. and below.

26. The process of claim 19 wherein the condenser is maintained at a temperature of about −20° C. to about −30° C.

27. The process of claim 19 wherein acetic acid is introduced below the stream of methyltrichlorosilane into the reboiler.

28. The process of claim 19 wherein acetic acid is introduced below the stream of methyltrichlorosilane into the heated column.

29. The process of claim 19 further comprising heating acetic acid to form acetic acid vapor and introducing acetic acid vapor.

* * * * *